(12) United States Patent
Kishawi et al.

(10) Patent No.: US 8,380,318 B2
(45) Date of Patent: Feb. 19, 2013

(54) PAIN MANAGEMENT WITH STIMULATION SUBTHRESHOLD TO PARESTHESIA

(75) Inventors: Eyad Kishawi, San Carlos, CA (US); Jeffery M. Kramer, San Francisco, CA (US)

(73) Assignee: Spinal Modulation, Inc., Menlo Park, CA (US)

( * ) Notice: Subject to any disclaimer, the term of this patent is extended or adjusted under 35 U.S.C. 154(b) by 131 days.

(21) Appl. No.: 12/730,908

(22) Filed: Mar. 24, 2010

(65) Prior Publication Data

US 2010/0249875 A1    Sep. 30, 2010

Related U.S. Application Data

(60) Provisional application No. 61/163,007, filed on Mar. 24, 2009.

(51) Int. Cl.
    *A61N 1/00* (2006.01)
(52) U.S. Cl. ........................................... 607/46
(58) Field of Classification Search ............... 607/46, 607/117
    See application file for complete search history.

(56) References Cited

U.S. PATENT DOCUMENTS

| | | |
|---|---|---|
| 525,891 A | 9/1894 | Fricke |
| 3,724,467 A | 4/1973 | Avery et al. |
| 3,845,770 A | 11/1974 | Theeuwes et al. |
| 3,916,899 A | 11/1975 | Theeuwes et al. |
| 4,141,367 A | 2/1979 | Ferreira |
| 4,232,679 A | 11/1980 | Schulman |
| 4,298,003 A | 11/1981 | Theeuwes et al. |
| 4,313,448 A | 2/1982 | Stokes |
| 4,374,527 A | 2/1983 | Iversen |
| 4,479,491 A | 10/1984 | Martin |
| 4,573,481 A | 3/1986 | Bullara |
| 4,577,642 A | 3/1986 | Stokes |
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,920,979 A | 5/1990 | Bullara |
| 4,940,065 A | 7/1990 | Tanagho et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,358,514 A | 10/1994 | Schulman et al. |

(Continued)

FOREIGN PATENT DOCUMENTS

| | | |
|---|---|---|
| CN | 2401143 Y | 10/2000 |
| EP | 0779080 A | 6/1997 |

(Continued)

OTHER PUBLICATIONS

Abdulla et al.; Axotomy- and autotomy-induced changes in the excitability of rat dorsal root ganglion neurons; J Neurophysiol; 85(2); pp. 630-643, Feb. 2001.

(Continued)

*Primary Examiner* — Scott Getzow
(74) *Attorney, Agent, or Firm* — Shay Glenn LLP

(57) ABSTRACT

Devices, systems and methods are provided for treating pain while minimizing or eliminating possible complications and undesired side effects, particularly the sensation of paresthesia. This is achieved by stimulating in proximity to a dorsal root ganglion with stimulation energy in a manner that will affect pain sensations without generating substantial sensations of paresthesia. In some embodiments, such neurostimulation takes advantage of anatomical features and functions particular to the dorsal root ganglion.

22 Claims, 9 Drawing Sheets

U.S. PATENT DOCUMENTS

| | | |
|---|---|---|
| 5,370,644 A | 12/1994 | Langberg |
| 5,411,537 A | 5/1995 | Munshi et al. |
| 5,417,719 A | 5/1995 | Hull et al. |
| 5,489,294 A | 2/1996 | McVenes et al. |
| 5,505,201 A | 4/1996 | Grill et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,733,322 A | 3/1998 | Starkebaum |
| 5,741,319 A | 4/1998 | Woloszko et al. |
| 5,755,750 A | 5/1998 | Petruska et al. |
| 5,807,339 A | 9/1998 | Bostrom et al. |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,983,141 A | 11/1999 | Sluijter et al. |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 | 10/2001 | Meyer |
| 6,314,325 B1 | 11/2001 | Fitz |
| 6,319,241 B1 | 11/2001 | King et al. |
| 6,349,233 B1 | 2/2002 | Adams |
| 6,353,762 B1 | 3/2002 | Baudino et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,971,391 B1 | 12/2005 | Wang et al. |
| 6,978,180 B2 | 12/2005 | Tadlock |
| 7,096,070 B1 | 8/2006 | Jenkins et al. |
| 7,127,287 B2 | 10/2006 | Duncan et al. |
| 7,333,857 B2 | 2/2008 | Campbell |
| 7,337,005 B2 | 2/2008 | Kim et al. |
| 7,337,006 B2 | 2/2008 | Kim et al. |
| 7,447,546 B2 | 11/2008 | Kim et al. |
| 7,450,993 B2 | 11/2008 | Kim et al. |
| 7,502,651 B2 | 3/2009 | Kim et al. |
| 7,580,753 B2 | 8/2009 | Kim et al. |
| 2001/0003799 A1 | 6/2001 | Boveja |
| 2002/0077684 A1 | 6/2002 | Clemens et al. |
| 2002/0116030 A1 | 8/2002 | Rezai |
| 2002/0128694 A1 | 9/2002 | Holsheimer |
| 2002/0147486 A1 | 10/2002 | Soukup et al. |
| 2003/0018367 A1 | 1/2003 | DiLorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0088301 A1 | 5/2003 | King |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2004/0015202 A1 | 1/2004 | Chandler et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0172089 A1 | 9/2004 | Whitehurst et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052827 A1 | 3/2006 | Kim et al. |
| 2006/0052836 A1 | 3/2006 | Kim et al. |
| 2006/0052856 A1 * | 3/2006 | Kim et al. ............ 607/117 |
| 2006/0064150 A1 | 3/2006 | Heist et al. |
| 2006/0089609 A1 | 4/2006 | Bleich et al. |
| 2006/0095088 A1 | 5/2006 | DeRidder |
| 2006/0155344 A1 | 7/2006 | Rezai et al. |
| 2006/0195169 A1 | 8/2006 | Gross et al. |
| 2006/0206118 A1 | 9/2006 | Kim et al. |
| 2006/0241716 A1 | 10/2006 | Finch et al. |
| 2007/0060954 A1 * | 3/2007 | Cameron et al. ............ 607/2 |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0140152 A1 | 6/2008 | Imran et al. |
| 2008/0140153 A1 | 6/2008 | Burdulis |
| 2008/0140169 A1 | 6/2008 | Imran |
| 2008/0147156 A1 | 6/2008 | Imran |

| | | | |
|---|---|---|---|
| 2008/0167698 | A1 | 7/2008 | Kim et al. |
| 2008/0183221 | A1 | 7/2008 | Burdulis |
| 2008/0183257 | A1 | 7/2008 | Imran et al. |
| 2008/0188916 | A1 | 8/2008 | Jones et al. |
| 2009/0210041 | A1 | 8/2009 | Kim et al. |
| 2009/0248095 | A1 | 10/2009 | Schleicher et al. |
| 2010/0121408 | A1 | 5/2010 | Imran et al. |
| 2011/0257693 | A1 | 10/2011 | Burdulis |
| 2011/0276056 | A1 | 11/2011 | Grigsby et al. |
| 2012/0158094 | A1 | 6/2012 | Kramer et al. |
| 2012/0197370 | A1 | 8/2012 | Kim et al. |

FOREIGN PATENT DOCUMENTS

| | | |
|---|---|---|
| EP | 1304135 A2 | 4/2003 |
| JP | 8080353 A | 3/1996 |
| JP | 10243954 A | 9/1998 |
| JP | 2004512105 | 4/2004 |
| JP | 2005516697 | 6/2005 |
| WO | WO 02/096512 A1 | 12/2002 |
| WO | WO 03/063692 | 8/2003 |
| WO | WO 03/066154 A2 | 8/2003 |
| WO | WO 03/090599 A2 | 11/2003 |
| WO | WO 2005/092432 A1 | 10/2005 |
| WO | WO 2006/084635 A2 | 8/2006 |

OTHER PUBLICATIONS

Advanced Neuromodulation Systems, Inc. (ANSI) Research Briefing dated Aug. 20, 2004 by Stephens Inc. Investment Bankers pp. 1-4.
Advanced Neuromodulation Systems, Inc. (ANSI) Research Bulletin dated Jul. 2, 2004 by Stephens Inc. Investment Bankers pp. 1-7.
Advanced Neuromodulation Systems, Inc. (ANSI) Research Bulletin dated Jul. 27, 2004 by Stephens Inc. Investment Bankers pp. 1-9.
Advanced Neuromodulation Systems, Inc. Equity Research dated Jan. 16, 2003 by Pacific Growth Equities pp. 1-8.
Alo, Kenneth M. 2002. New Trends in Neuromodulation for the Management of Neuropathic Pain. Neurosurgery. 50 (4): 690-703.
Aoki, Yasuchika et al. 2004. Distribution and Immunocytochemical Characterization of Dorsal Root Ganglion Neurons Innervating the Lumbar Intervertebral Disc in Rats: A Review. Life Sciences. 74 (21): 2627-2642.
Askar, Zahid, et al. 2003. Scott Wiring for Direct Repair of Lumbar Spondylolysis. Spine. 28 (4): 354-357.
Baba, Hiroshi et al. 1999. Peripheral Inflammation Facilitates A? Fiber-Mediated Synaptic Input to the Substantia Gelatinosa of the Adult Rat Spinal Cord. The Journal of Neuroscience. 19 (2): 859-867.
Bajwa, Zahid H. et al. 2001. Herpetic Neuralgia: Use of Combination Therapy for Pain Relief in Acute and Chronic Herpes Zoster. Geriatrics. 56 (12): 18-24.
Barendse, G.A. et al. 2001. Randomized Controlled Trial of Percutaneo Intradiscal Radiofrequency Thermocoagulation for Chronic Discogenic Back Pain: Lack of Effect From a 90-Second 70 C Lesion. Spine. 26 (3): 287-92. (Abstract Only).
Barlocher, C.B. et al. 2003. Kryorhizotomy: An Alternative Technique for Lumbar Medial Branch Rhizotomy in Lumbar Facet Syndrome. J Neurosurg. 98 (1): 14-20. (Abstract Only).
Blau, A. et al. 1997. Characterization and Optimization of Microelectrode Arrays for In Vivo Nerve Signal Recording and Stimulation. Biosens Bioelectron.12 (9-10): 883-92. (Abstract Only).
Boston Scientific a Neuromodulation Primer dated Jun. 9, 2004 in Medical Supplies and Devices, published by Susquehanna Financial Group, LLLP pp. 1-17.
Brammah, T.B. et al. 1994. Syringomyelia as a Complication of Spinal Arachnoiditis. Spine. 19 (22): 2603-5. (Abstract Only).
Braverman D.L. et al. 2001. Using Gabapentin to Treat Failed Back Surgery Syndrome Caused by Epidural Fibrosis: A Report of 2 Cases. Arch Phys Med Rehabil. 82 (5): 691-3. (Abstract Only).
Burton et al.; The organization of the seventh lumbar spinal ganglion of the cat; J Comp Neurol.; 149(2); pp. 215-232; May 15, 1973.
Carlton, Susan M. et al. 2001. Tonic Control of Peripheral Cutaneo Nociceptors by Somatostatin Receptors. Journal of Neuroscience. 21 (11): 4042-4049.
Chaplan, S.R. et al. 1994. Quantitative Assessment of Tactile Allodynia in the Rat Paw. Journal of Neuroscience Methods. 53 (1): 55-63.
Cho, J. 1997. Percutaneo Radiofrequency Lumbar Facet Rhizotomy in Mechanical Low Back Pain Syndrome. Stereotact Funct Neurosurg. 68 (1-4): 212-7. (Abstract Only).
Crampon, M.-A. et al. 2002. Nerve Cuff Electrode With Shape Memory Alloy Armature: Design and Fabrication. Bio-Medical Materials and Engineering. 12 (4): 397-410.
Cuoco, Jr., Frank A. et al. 2000. Measurement of External Pressures Generated by nerve Cuff Electrodes. IEEE Transactions on Rehabilitation Egineering. 8 (1): 35-41.
Cyberonics, Inc. Equity Research dated Jan. 16, 2003 by Pacific Growth Equities pp. 1-14.
Denny, N.M. et al. 2003. Evaluation of an Insulated Tuohy Needle System for the Placement of Interscalene Brachial Plex Catheters. Anaesthesia. 58 (6): 554-7. (Abstract Only).
Dreyfuss, Paul et al. 2000. Efficacy and Validity of Radiofrequency Neurotomy for Chronic Lumbar Zygapophysial Joint Pain. Spine. 25 (10): 1270-1277.
Dubuisson, D. 1995. Treatment of Occipital Neuralgia by Partial Posterior Rhizotomy at C1-3. J Neurosurg. 82 (4): 581-6. (Abstract Only).
Eschenfelder, Sebastian et al. 2000. Dorsal Root Section Elicits Signs of Neuropathic Pain Rather than Reversing Them in Rats With L5 Spinal Nerve Injury. Pain. 87 (2): 213-219.
Firth, Ava et al. 1999. Development of a Scale to Evaluate Postoperative Pain in Dogs. J Am Vet Med Assoc. 214 (5): 651-659.
Garcia Cosamalon, P. J. et al. 1991. Dorsal Percutaneo Radiofrequency Rhizotomy Guided With CT Scan in Intercostal Neuralgias. Technical note. Acta Neurochir (Wien). 109 (3-4): 140-1.
Giorgi, C. et al. 1984. Surgical Treatment of Glossopharyngeal Neuralgia and Pain From Cancer of the Nasopharynx. A 20-Year Experience. J Neurosurg. 61 (5): 952-5. (Abs. Only).
Gocer, A.I. et al. 1997. Percutaneo Radiofrequency Rhizotomy of Lumbar Spinal Facets the Results of 46 cases. Neurosurg Rev. 20 (2): 114-6. (Abstract Only).
Haller, H. et al. Treatment of Chronic Neuropathic Pain After Traumatic Central Cervical Cord Lesion with Gabapentin. Journal of Neural Transmission. 110 (9): 977-981.
Herron, L.D. 1989. Selective Nerve Root Block in Patient Selection for Lumbar Surgery: Surgical Results. J Spinal Disord. 2 (2): 75-9. (Abstract Only).
Higuchi, Yoshinori, et al. 2002. Exposure of the Dorsal Root Ganglion in Rats to Pulsed Radiofrequency Currents Activates Dorsal Horn Lamina I and II Neurons. Neurosurgery. 50 (4): 850-856.
Holsheimer, J. et al. 1995. Effects of Electrode Geometry and Combination on Nerve Fibre Selectivity in Spinal Cord Stimulation. Medical & Biological Engineering & Computing. 33 (5): 676-682.
Igarashi, T. et al. 2004. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-.
Julius, David et al. 2001. Molecular Mechanisms of Nociception. Nature. 413 (6852): 203-210.
Kanpolat, Yucel et al. 2001. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534.
Kapadia, N. P. et al. 2000. Gabapentin for Chronic Pain in Spinal Cord Injury: A Case Report. Arch Phys Med Rehabil. 81 (10): 1439-41. (Abstract Only).
Kapoor, Vibhu et al. 2003. Refractory Occipital Neuralgia: Preoperative Assessment With CT-Guided Nerve Block Prior to Dorsal Cervical Rhizotomy. American Journal of Neuroradiology. 24 (10): 2105-10.
Karai, Laszlo et al. 2004. Deletion of Vanilloid Receptor 1-Expressing Primary Afferent Neurons for Pain Control. Journal of Clinical Investigation. 113 (9): 1344-1352.
Kline, David G. et al. 1998. Management and Results of Sciatic Nerve Injuries: a 24-Year Experience. Journal of Neurosurgery. 89 (1): 13-23.

Kobayashi, Shigeru et al. 2004. Pathology of Lumbar Nerve Root Compression Part 1: Intraradicular Inflammatory Changes Induced by Mechanical Compression. Journal of Orthopaedic Research. 22 (1): 170-179.

Kobayashi, Shigeru et al. 2004. Pathology of Lumbar Nerve Root Compression Part 2: Morphological and Immunohistochemical Changes of Dorsal Root Ganglion. Journal of Orthopaedic Research. 22 (1): 180-188.

Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.

Koszewski, W. et al. 2003. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only).

Lawrence, Stephen M. et al. 2002. Long-Term Biocompatibility of Implanted Polymer-Based Intrafascicular Electrodes. Journal of Biomedical Materials Research. 63 (5): 501-506.

Lee, In-Seop et al. 2002. Characterization of Iridium Film as a Stimulating Neural Electrode. Biomaterials. 23 (11): 2375-2380.

Lew, Henry L. et al. 2004. Preganglionic Approach to Transforaminal Epidural Steroid Injections. Am. J. Phys. Med. Rehabil. 83 (5): 378.

Lopez et al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; 2001.

Ma et al.; Enhanced excitability of dissociated primary sensory neurons after chronic compression of the dorsal root ganglion in the rat; Pain; 113(1-2); pp. 106-112; Jan. 2005.

Maher, C.O. et al. 1999. Lateral Exit-Zone Stenosis and Lumbar Radiculopathy. J Neurosurg. 90 (1): 52-8. (Abstract Only).

Mailley, Sophie et al. 2004. Thin Film Platinum Cuff Electrodes for Neurostimulation: In Vitro Approach of Safe Neurostimulation Parameters. Bioelectrochemistry. 63: 359-364.

Masini, Michelle et al. 1996. Activated Pyrolytic Carbon Tip Pacing Leads: An Alternative to Steroid-Eluting Pacing Leads? PACE. 1: 1832-1835.

Medtronic, Inc. Equity Research dated Dec. 18, 2002 by Pacific Growth Equities pp. 1-20.

Medtronic. Analysis of Sales/Earnings-F1Q05: Many Gives and Takes in the Quarter dated Aug. 20, 2004 by Morgan Stanley pp. 1-25.

Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.

Modern Ideas: The Gate Control Theory of Chronic Pain. SpineHealth.com: Your Comprehensive Resource for Back Pain. http://www.spine-health.com/topics/cd/pain/chronic_pain_theories/chronic_pain_theory02.html (accessed Feb. 24, 2006).

Mond, Harry G. et al. 2004. Implantable Transveno Pacing Leads: The Shape of Things to Come. PACE. 27: 887-893.

Monti, Enrico. 2004. Peripheral Nerve Stimulation: A Percutaneo Minimally Invasive Approach. Neuromodulation. 7 (3): 193. (Abstract Only).

Myles et al.; Effects of different methods of peripheral nerve repair on the number and distribution of muscle afferent neurons in rat dorsal root ganglion; J Neurosurg; 77(3); pp. 457-462; Sep. 1992.

Nannini et al.; Muscle recruitment with intrafascicular electrodes; IEEE Trans on Biomedical Engineering; vol. 38; No. 8; pp. 769-776 Aug. 1991.

Naples, Gregory G. 1988. A Spiral Nerve Cuff Electrode for Peripheral Nerve Stimulation. IEEE Transactions on Biomedical Engineering. 35 (11): 905-916.

Narozny, Martin et al. 2001. Therapeutic Efficacy of Selective Nerve Root Blocks in the Treatment of Lumbar Radicular Leg Pain. Swiss Med Wkly. 131 (5-6): 75-80.

Nashold, Blaine S. et al. 1979. Peripheral Nerve Stimulation for Pain Relief Using a Multicontact Electrode System. Technical note. Journal of Neurosurgery. 51 (6): 872-873.

Nashold, Blaine S. et al. 1982. Long-Term Pain Control by Direct Peripheral-Nerve Stimulation. The Journal of Bone and Joint Surgery. 64 (1): 1-10.

Neumann, Simona et al. 2002. Regeneration of Sensory Axons Within the Injured Spinal Cord Induced by Intraganglionic cAMP Elevation. Neuron. 34 (6): 885-93.

Nielson, K.D. et al. 1976. Peripheral Nerve Injury From Implantation of Chronic Stimulating Electrodes for Pain Control. Surg Neurol. 5 (1): 51-3. (Abstract Only).

North, Richard B. et al. 1991. Dorsal Root Ganglionectomy for Failed Back Surgery Syndrome: A 5-Year Follow-Up Study. J Neurosurg. 74: 236-242.

North, Richard B. et al. 2000. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company.

Nygaard, Oystein P. et al. 1998. The Function of Sensory Nerve Fibers in Lumbar Radiculopathy: Use of Quantitative Sensory Testing in the Exploration of Different Populations of Nerve Fibers and Dermatomes. Spine. 23 (3): 348-352.

Obata, K. et al. 2004. Activation of Extracellular Signal-Regulated Protein Kinase in the Dorsal Root Ganglion Following Inflammation Near the Nerve Cell Body. Neuroscience. 126 (4): 1011-1021.

Obata, Koichi, et al. 2002. Expression of Neurotrophic Factors in the Dorsal Root Ganglion in a Rat Model of Lumbar Disc Herniation. Pain. 99 (1-2): 121-132.

Olby, Natasha J. et al. 2001. Development of a Functional Scoring System in Dogs With Acute Spinal Cord Injuries. Am J Vet Res. 62 (10): 1624-1628.

Parlier-Cuau, Caroline et al. 1999. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513.

Pedrolli, C. et al. 1990. [Dorsolumbar Arachnoid Cysts. A Case Report]. Recenti Prog Med. 81 (11): 699-701. (Abstract Only).

Prats-Galino et al.; Representations of hindlimb digits in rat dorsal root ganglia; J Comp Neurol; 408(1); pp. 137-145; May 24 1999.

Rodriguez, Francisco J. et al. 2000. Polyimide Cuff Electrodes for Peripheral Nerve Stimulation. Journal of Neuroscience Methods. 98 (2): 105-118.

Rokugo, Tomoyuki et al. 2002. A Histochemical Study of Substance P in the Rat Spinal Cord: Effect of Transcutaneo Electrical Nerve Stimulation. J Nippon Med Sch. 69 (5): 428-433.

Romero, E. et al. 2001. Neural Morphological Effects of Long-Term Implantation of the Self-Sizing Spiral Cuff Nerve Electrode. Medical & Biological Engineering & Computing. 39 (1): 90-100.

Rongstad, K. et al. 1996. Popliteal Sciatic Nerve Block for Postoperative Analgesia. Foot Ankle Int. 17 (7): 378-82. (Abstract Only).

Ruetten, S. et al. 2003. Endoscopic Surgery of the Lumbar Epidural Space (Epiduroscopy): Results of Therapeutic Intervention in 93 Patients. Minim Invasive Neurosurg. 46 (1): 1-4. (Abstract Only).

Sairyo, K. et al. 2003. A New Endoscopic Technique to Decompress Lumbar Nerve Roots Affected by Spondylolysis. Technical Note. J Neurosurg. 98 (3): 290-3. (Abstract Only).

Salame, K. et al. 2003. Surgical Treatment of Spasticity by Selective Posterior Rhizotomy 30 Years Experience. Isr Med Assoc J. 5 (8): 543-6. (Abstract Only).

Saris, S.C. et al. 1986. Sacrococcygeal Rhizotomy for Perineal Pain. Neurosurgery. 19 (5): 789-93. (Abstract Only).

Sauvage, P.J. et al. 2000. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De.

Schwartzman, Robert J. et al. 2001. Neuropathic Central Pain: Epidemiology, Etiology, and Treatment Options. Arch Neurol. 58 (10): 1547-1550.

Sedan, R. et al. 1978. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125.

Sheth, Rishi N. et al. 2002. Mechanical Hyperalgesia After an L5 Ventral Rhizotomy or an L5 Ganglionectomy in the Rat. Pain. 96: 63-72.

Siddall, Philip J. et al. 2004. Persistent Pain as a Disease Entity: Implications for Clinical Management. Anesth Analg. 99: 510-20.

Silvers, H.R. 1990. Lumbar Percutaneo Facet Rhizotomy. Spine.15 (1): 36-40. (Abstract Only).

Slappendel, R. et al. 1997. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. (Abstract Only).

Sluijter, Menno E. et al. 1998. The Effects of Pulsed Radiofrequency Fields Applied to the Dorsal Root Ganglion—A Preliminary Report. The Pain Clinic.11 (2): 109-117.

Smith, H.P. et al. 1981. Radiofrequency Neurolysis in a Clinical Model: Neuropathological Correlation. J Neurosurg. 55 (2): 246-53. (Abstract Only).

Spaic, M. et al. 1999. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312.

Spaic, M. et al. 2002. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462.

Stanton-Hicks, M. et al. 1997. Stimulation of the Central and Peripheral Nervo System for the Control of Pain. Journal of Clinical Neurophysiology. 14 (1): 46-62.

Steinbok, P. et al. 1998. Complications After Selective Posterior Rhizotomy for Spasticity in Children With Cerebral Palsy. Pediatr Neurosurg. 28 (6): 300-13. (Abstract Only).

Stolker, Robert J. et al. 1994. The Treatment of Chronic Thoracic Segmental Pain by Radiofrequency Percutaneo Partial Rhizotomy. J Neurosurg. 80 : 986-992.

Strait, T.A. et al. 1981. Intraspinal Extradural Sensory Rhizotomy in Patients With Failure of Lumbar Disc Surgery. J Neurosurg. 54 (2): 193-6. (Abstract Only).

Taha, J.M. et al. 1995. Long-Term Results of Radiofrequency Rhizotomy in the Treatment of Cluster Headache. Headache. 35 (4): 193-6. (Abstract Only).

Taub, Arthur et al. 1995. Dorsal Root Ganglionectomy for Intractable Monoradicular Sciatica: A Series of 61 Patients. Stereotact Funct Neurosurg. 65 (1-4): 106-110.

Uematsu, Sumio. 1988. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). P.

Van Zundert, Jan et al. 2005. Pulsed Radiofrequency in Chronic Pain Management: Looking for the Best Use of Electrical Current. World Institute of Pain. 5 (2): 74-76.

Van De Kraats, Everine B. et al. 2004. Noninvasive Magnetic Resonance to Three-Dimensional Rotational X-Ray Registration of Vertebral Bodies for Image-Guided Spine Surgery. Spine. 29 (3): 293-297.

Van Kleef, M. et al. 1993. Effects and Side Effects of a Percutaneo Thermal Lesion of the Dorsal Root Ganglion in Patients with Cervical Pain Syndrome. Pain. 52 (1): 49-53.

Van Kleef, M. et al. 1996. Radiofrequency Lesion Adjacent to the Dorsal Root Ganglion for Cervicobrachial Pain: A Prospective Double Blind Randomized Study. Neurosurgery. 38 (6): 1127-31.

Van Kleef, Maarten et al. 1998. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill.

Van Zundert, J. et al. 2005. Pulsed and Continuo Radiofrequency Current Adjacent to the Cervical Dorsal Root Ganglion of the Rat Induces Late Cellular Activity in the Dorsal Horn. Anesthesiology. 102 (1): 125-31.

Vaughan, R. 1975. Percutaneo Radiofrequency Gangliotomy in the Treatment of Trigeminal Neuralgia and Other Facial Pain. Aust N Z J Surg. 45 (2): 203-7. (Abstract Only).

Viton, J.-M. et al. 1998. Short-Term Assessment of Periradicular Corticosteroid Injections in Lumbar Radiculopathy Associated With Disc Pathology. Neuroradiology. 40 (1): 59-62.

Viton, J.M. et al. 1998. Short-Term Evaluation of Periradicular Corticosteroid Injections in the Treatment of Lumbar Radiculopathy Associated With Disc Disease. Rev Rhum Engl Ed. 65 (3): 195-200. (Abstract Only).

Wagner, A.L. et al. 2002. Selective Nerve Root Blocks. Tech Vasc Interv Radiol. 5 (4): 194-200. (Abstract Only).

Waxman et al.; Sodium channels, excitability of primary sensory neurons, and the molecular basis of pain; Muscle Nerve; 22(9); pp. 1177-1187; Sep. 1999.

Weiner, Richard L. 2000. The Future of Peripheral Nerve Neurostimulation. Neurological Research. 22 (3): 299-304.

Weiner, Richard L. 2003. Peripheral Nerve Neurostimulation. Neurosurgery Clinics of North America. 14 (3): 401-408.

Weinstein, James et al. 1988. The Pain of Discography. Spine. 13 (12):1344-8.

Wessels et al.; A rostrocaudal somatotopic organization in the brachial dorsal root ganglia of neonatal rats; Clin Neurol Neurosurg; 95 Suppl; pp. S3-S11; 1993.

Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.

Wessels et al.; Somatotopic organization in the sensory innervation of the rat hindlimb during development, using half dorsal root ganglia as subsegmental units; Eur J Morphol; 28(2-4); pp. 394-403; 1990.

Wessels et al.; The rostrocaudal organization in the dorsal root ganglia of the rat: a consequence of plexus formation?; Anat Embryol (Berl); 190(1); pp. 1-11; Jul. 1994.

Wetzel, F. Todd et al. 1997. Extradural Sensory Rhizotomy in the Management of Chronic Lumbar Radiculopathy: A Minimum 2-Year Follow-up Study. Spine. 22 (19): 2283-2291.

Wetzel, F.T. 1992. Chronic Benign Cervical Pain Syndromes: Surgical Considerations. Spine. 17 (10): S367-74. (Abstract Only).

Wetzel, F.T. et al. 1992. The Treatment of Chronic Extremity Pain in Failed Lumbar Surgery. The Role of Lumbar Sympathectomy. Spine. 17 (12): 2367-8. (Abstract Only).

White, P.F. et al. 2003. The Use of a Continuo Popliteal Sciatic Nerve Block After Surgery Involving the Foot and Ankle: Does It Improve the Quality of Recovery? Anesth Analg. 97 (5): 1303-9. (Abstract Only).

Whitworth, Louis Anthony et al. 2002. Application of Spinal Ablative Techniques for the Treatment of Benign Chronic Painful Conditions. Spine. 27 (22): 2607-2612.

Wilkinson, H.A. et al. 2001. Sensory Ganglionectomy: Theory, Technical Aspects, and Clinical Experience. J Neurosurg. 95 (1): 61-6. (Abstract Only).

Wong, C.B. et al. 2002. Clinical Outcomes of Revision Lumbar Spinal Surgery: 124 Patient With a Minimum of Two Years of Follow-Up. Chang Gung Med J. 25 (3): 175-82. (Abstract Only).

Wright, Robert E. et al. 1998. Neurostimulation of the L2 Dorsal Root Ganglion for Intractable Disc Pain: Description of a Novel Technique. Presented at the IFESS.

Wu, Gang et al. 2001. Early Onset of Spontaneo Activity in Uninjured C-Fiber Nociceptors After Injury to Neighboring Nerve Fibers. Journal of Neuroscience. 21 (8): RC140.

Yamashita, Toshihiko et al. 2002. A Quantitative Analysis of Sensory Function in Lumbar Radiculopathy Using Current Perception Threshold Testing. Spine. 27 (14): 1567-1570.

Yoshida, Hirotoshi et al. 1997. Lumbar Nerve Root Compression Caused by Lumbar Intraspinal Gas: Report of Three Cases. Spine.22 (3): 348-351.

Young, R.F. 1996. Chapter 161: Dorsal Rhizotomy and Dorsal Root Ganglionectomy (pp. 3442-3451). Neurological Surgery 4th Edition. (Julian R. Youmans ed.). Philadelphia: W.B. Saunders Company.

Imran et al.; U.S. Appl. No. 12/607,009 entitled "Selective stimulation systems and signal parameters for medical conditions," filed Oct. 27, 2009.

Linker et al.; U.S. Appl. No. 12/687,737 entitled "Stimulation leads, delivery systems and methods of use," filed Jan. 14, 2010.

Brounstein et al.; U.S. Appl. No. 12/780,696 entitled "Methods, systems and devices for neuromodulating spinal anatomy," filed May 14, 2010.

Kramer et al.; U.S. Appl. No. 13/458,697 entitled "Selective stimulation to modulate the sympathetic nervous system," filed Apr. 27, 2012.

Kim et al.; U.S. Appl. No. 13/550,439 entitled "Methods for Stimulating a Dorsal Root Ganglion," filed Jul. 16, 2012.

Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.

* cited by examiner

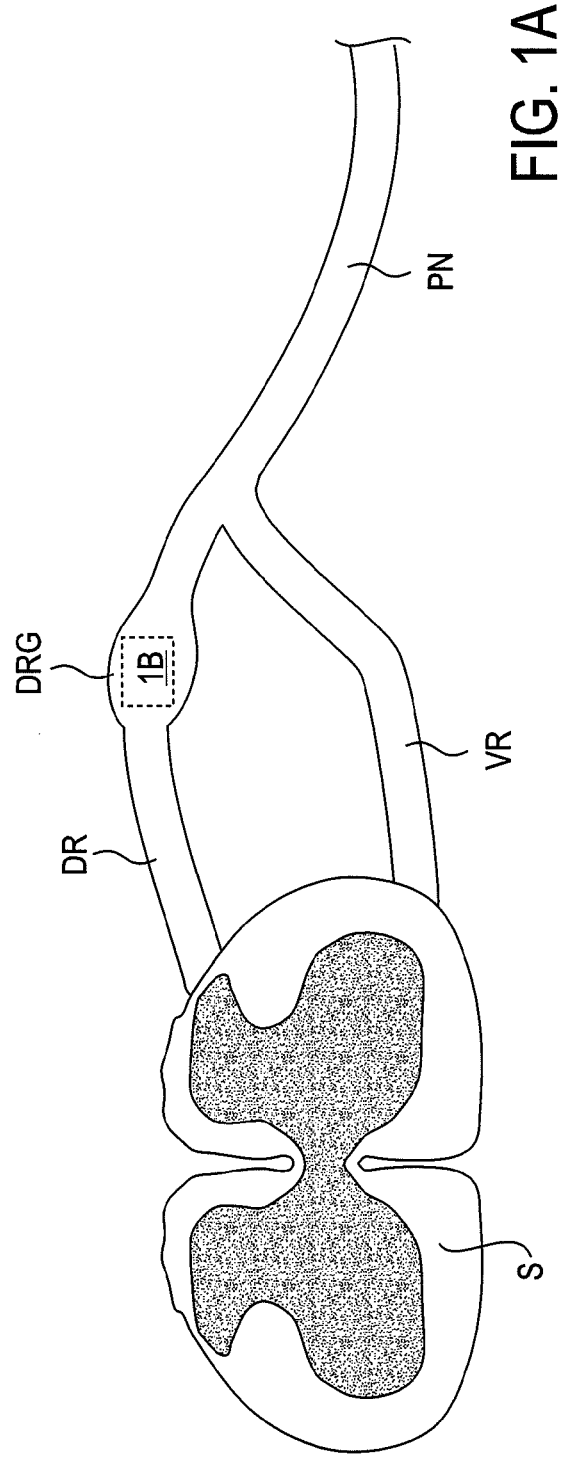
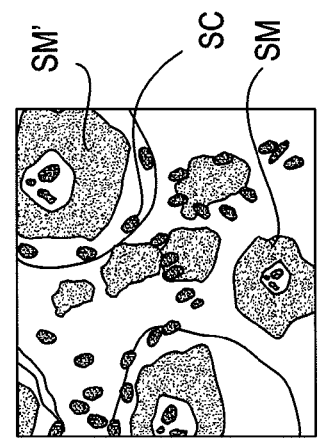
FIG. 1A
FIG. 1B

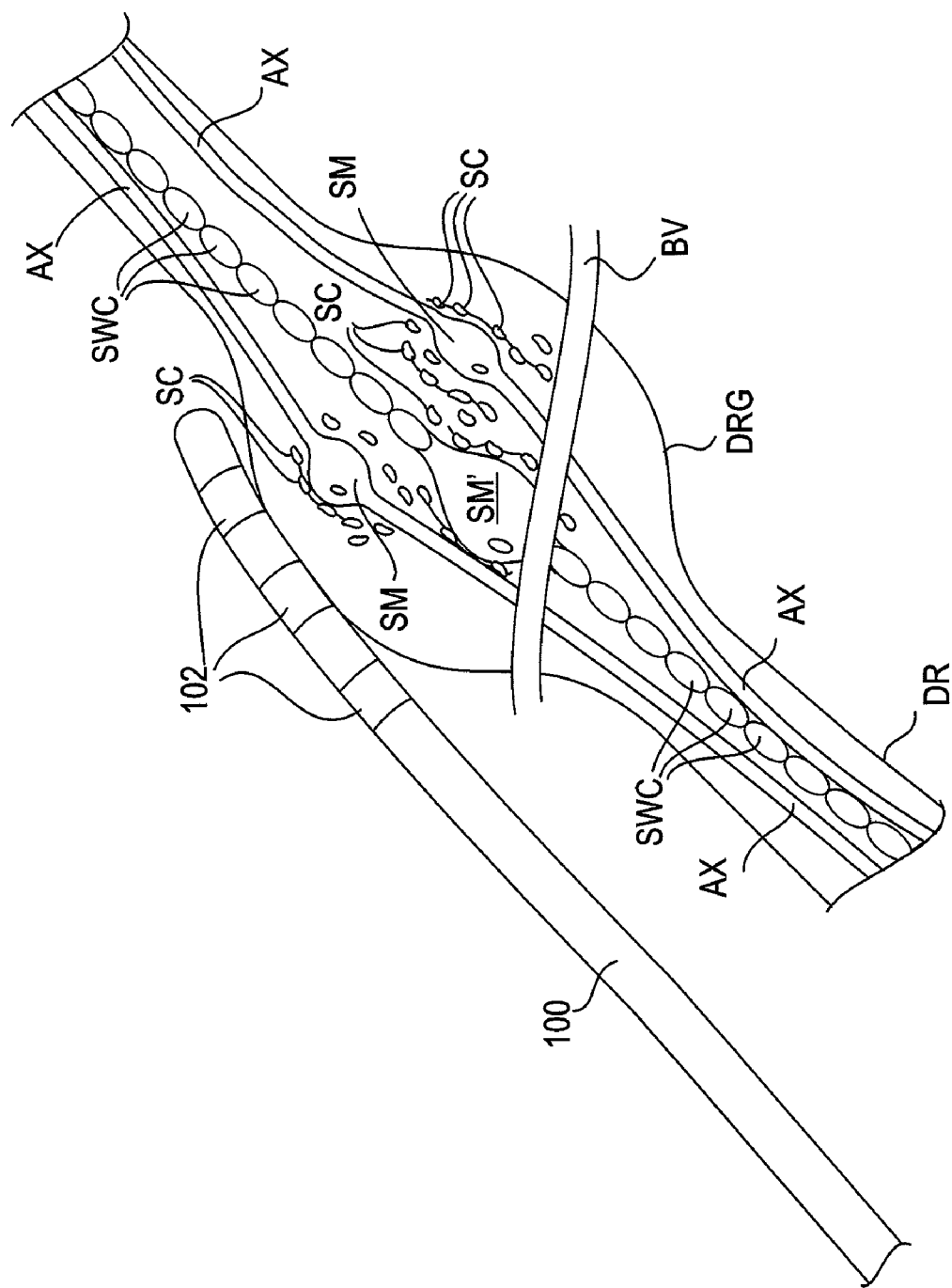

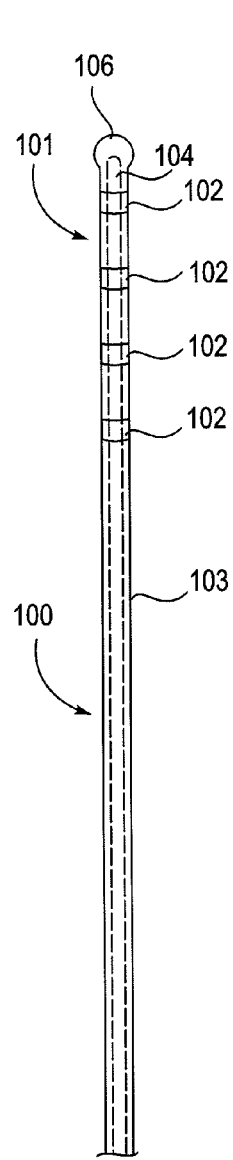 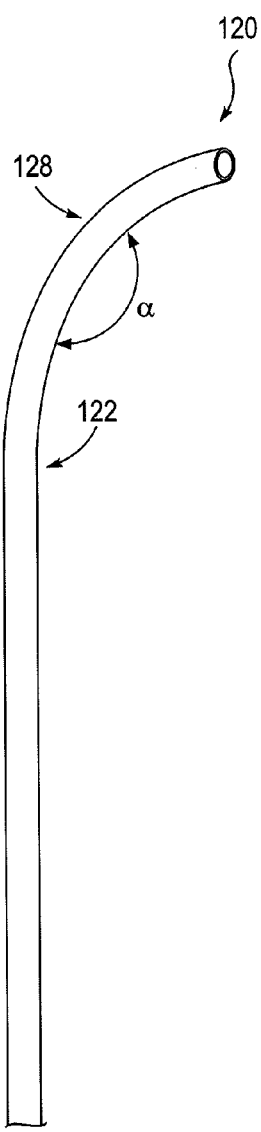 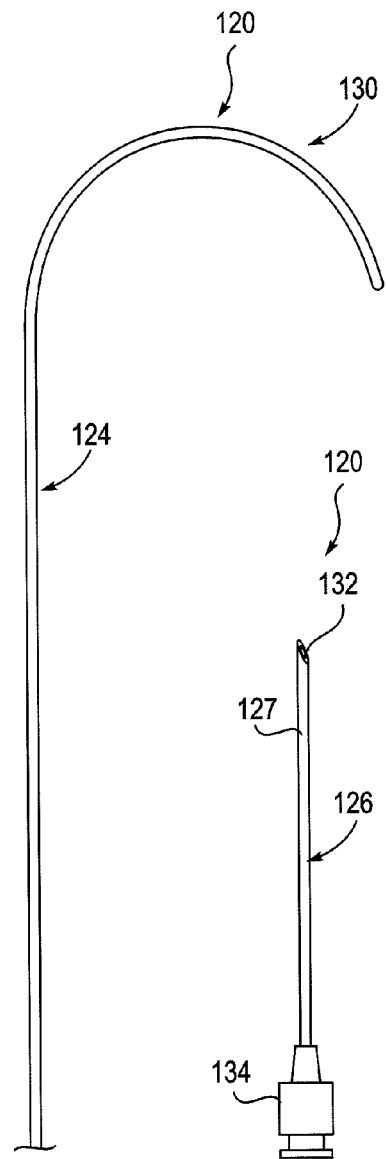
FIG. 10A    FIG. 10B    FIG. 10C    FIG. 10D

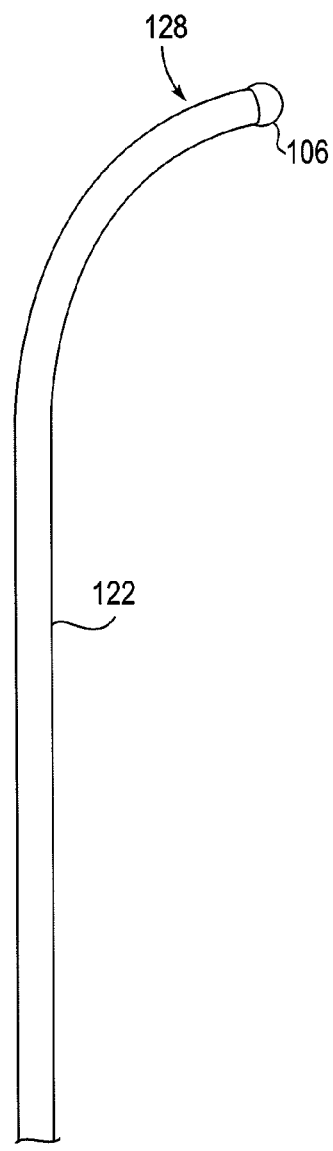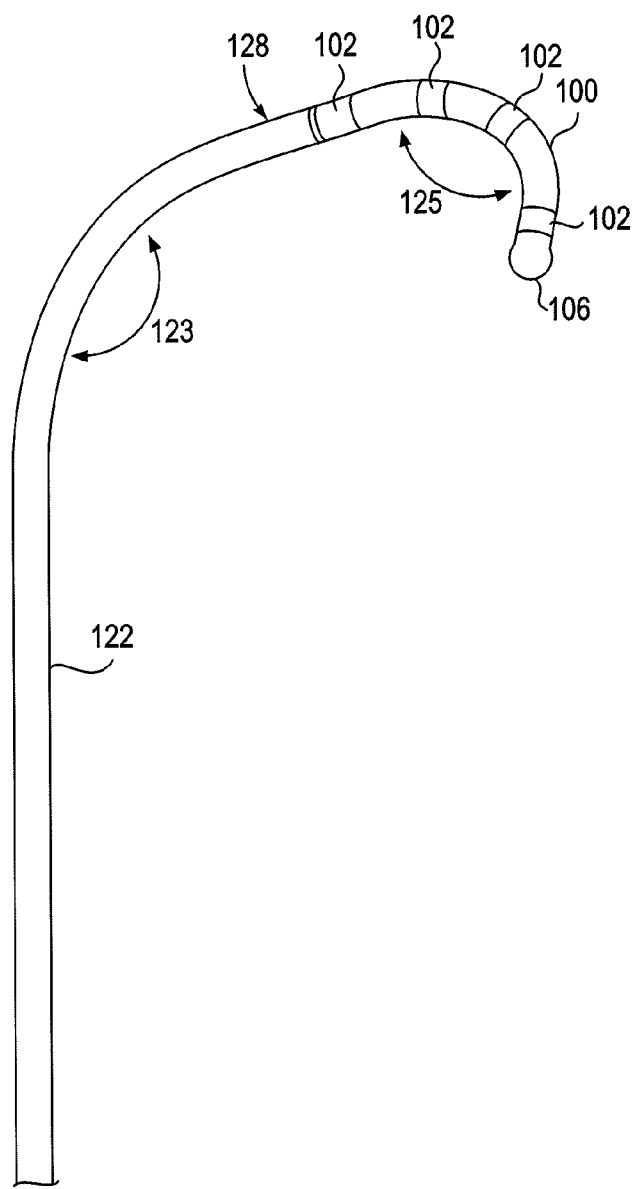
FIG. 11
FIG. 12

PAIN MANAGEMENT WITH STIMULATION SUBTHRESHOLD TO PARESTHESIA

CROSS-REFERENCES TO RELATED APPLICATION

This application claims priority under 35 U.S.C. 119(e) to U.S. Provisional Patent Application No. 61/163,007, entitled "Pain Management with Subthreshold Stimulation", filed Mar. 24, 2009, which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

For more than 30 years, spinal cord stimulation (SCS) has been used to treat a variety of pain syndromes. The goal of SCS is to create paresthesia that completely and consistently covers the painful areas, yet does not cause uncomfortable sensations in other areas. Paresthesia may be defined as a sensation of tingling, pricking, or numbness in an area of the body. It is more generally known as the feeling of "pins and needles". In some instances, the feeling of paresthesia is preferred over the feeling of pain. In SCS, paresthesia production is accomplished by stimulating $A\beta$ fibers in the dorsal column and/or the dorsal roots. Dorsal column stimulation typically causes paresthesia in several dermatomes at and below the level of the stimulator. In contrast, dorsal root stimulation activates fibers in a limited number of rootlets in close proximity to the stimulator and causes paresthesia in only a few dermatomes. Because of these factors, dorsal root stimulation with an SCS stimulator may not produce sufficient pain relief. In addition, stimulation of the roots with an SCS stimulator can cause uncomfortable sensations and motor responses. These side effects may occur at pulse amplitudes that are below the value needed for full paresthesia coverage. Therefore, the clinical goal of SCS is to produce an electrical field that stimulates the relevant spinal cord structures without stimulating the nearby nerve root.

Intraspinal nerve root stimulation is a technique related to SCS, except that electrodes are placed along the nerve rootlets in the lateral aspect of the spinal canal (this area is known as "the gutter"), rather than over the midline of the spinal cord. The electrodes are mounted on a cylindrical lead rather than on a traditional SCS paddle lead. The accuracy of the leads' placement within the gutter is confirmed by stimulating the nerve roots at perceptible levels, which result in paresthesia in the local area. Sensory paresthesia may be generated by stimulating at a level above the threshold for sensory recruitment. This may be used in conjunction with SCS to treat certain pain conditions.

For some patients, paresthesia is an undesired effect and is not a well tolerated alternative to pain. Therefore, improved treatments are needed to provide pain relief with minimal undesired effects. At least some of these objectives will be met by the present invention.

BRIEF SUMMARY OF THE INVENTION

The present invention provides devices, systems and methods for treating conditions, such as pain, while minimizing or eliminating possible complications and undesired side effects. In particular, the devices, systems and methods treat pain without generating substantial sensations of paresthesia. This is achieved by stimulating in proximity to a dorsal root ganglion with specific stimulation energy levels, as will be described in more detail herein.

In a first aspect of the present invention, a method is provided of treating pain in a patient comprising positioning a lead having at least one electrode disposed thereon so that at least one of the at least one electrode is in proximity to a dorsal root ganglion, and providing stimulation energy to the at least one of the at least one electrode so as to stimulate at least a portion of the dorsal root ganglion. Together the positioning of the lead step and the providing stimulation energy step affect pain sensations without generating substantial sensations of paresthesia.

In some embodiments, providing stimulation energy comprises providing stimulation energy at a level below a threshold for $A\beta$ fiber recruitment. And, in some embodiments, providing stimulation energy comprises providing stimulation energy at a level below a threshold for $A\beta$ fiber cell body recruitment.

In other embodiments, providing stimulation energy comprises: a) providing stimulation energy at a level above a threshold for $A\delta$ fiber cell body recruitment, b) providing stimulation energy at a level above a threshold for C fiber cell body recruitment, c) providing stimulation energy at a level above a threshold for small myelenated fiber cell body recruitment, or d) providing stimulation energy at a level above a threshold for unmyelenated fiber cell body recruitment.

In still other embodiments, providing stimulation energy comprises providing stimulation energy at a level which is capable of modulating glial cell function within the dorsal root ganglion. For example, in some embodiments, providing stimulation energy comprises providing stimulation energy at a level which is capable of modulating satellite cell function within the dorsal root ganglion. In other embodiments, providing stimulation energy comprises providing stimulation energy at a level which is capable of modulating Schwann cell function within the dorsal root ganglion.

In yet other embodiments, providing stimulation energy comprises providing stimulation energy at a level which is capable of causing at least one blood vessel associated with the dorsal root ganglion to release an agent or send a cell signal which affects a neuron or glial cell within the dorsal root ganglion.

In some embodiments, positioning the lead comprises advancing the lead through an epidural space so that at least a portion of the lead extends along a nerve root sleeve angulation. And, in some instances advancing the lead through the epidural space comprises advancing the lead in an antegrade direction.

In a second aspect of the present invention, a method is provided for treating a patient comprising selectively stimulating a small fiber cell body within a dorsal root ganglion of the patient while excluding an $A\beta$ fiber cell body with the dorsal root ganglion of the patient. In some embodiments, the small fiber body comprises an $A\delta$ fiber cell body. In other embodiments, the small fiber body comprises a C fiber cell body.

In a third aspect of the present invention, a method is provided for treating a patient comprising identifying a dorsal root ganglion associated with a sensation of pain by the patient, and neuromodulating at least one glial cell within the dorsal root ganglion so as to reduce the sensation of pain by the patient. In some embodiments, the at least one glial cell comprises a satellite cell. In other embodiments, the at least one glial cell comprises a Schwann cell. And, in some embodiments, neuromodulating comprises providing stimulation at a level that reduces the sensation of pain without generating substantial sensations of paresthesia.

In a fourth aspect of the present invention, a method is provided for treating a patient comprising positioning a lead having at least one electrode disposed thereon so that at least one of the at least one electrode is in proximity to a dorsal root ganglion, and providing stimulation energy to the at least one electrode so as to stimulate at least one blood vessel associated with the dorsal root ganglion in a manner that causes the at least one blood vessel to release an agent which neuromodulates a neuron within the dorsal root ganglion. In some embodiments, the agent comprises a neuromodulatory chemical that affects the function of neurons involved in pain sensory transduction.

In a fifth aspect of the present invention, a system is provided for treating pain in a patient comprising a lead having at least one electrode disposed thereon, wherein the lead is configured for placement in proximity to a dorsal root ganglion, and a pulse generator configured to provide stimulation energy to the at least one of the at least one electrode while the lead is positioned in proximity to the dorsal root ganglion so as to stimulate at least a portion of the dorsal root ganglion in a manner which affects pain sensations without generating substantial sensations of paresthesia.

In some embodiments, the pulse generator provides stimulation energy at a level at below a threshold for Aβ fiber recruitment. In other embodiments, the pulse generator provides stimulation energy at a level below a threshold for Aβ fiber cell body recruitment. In other embodiments, the pulse generator provides stimulation energy at a level above a threshold for Aδ fiber cell body recruitment. In still other embodiments, the pulse generator provides stimulation energy at a level above a threshold for C fiber cell body recruitment. In some embodiments, the pulse generator provides stimulation energy at a level above a threshold for small myelenated fiber cell body recruitment. And, in some embodiments, the pulse generator provides stimulation energy at a level above a threshold for unmyelenated fiber cell body recruitment.

In some embodiments, the pulse generator provides stimulation energy at a level which is capable of modulating glial cell function within the dorsal root ganglion. For example, in some embodiments, the pulse generator provides stimulation energy at a level which is capable of modulating satellite cell function within the dorsal root ganglion. In other embodiments, the pulse generator provides stimulation energy at a level which is capable of modulating Schwann cell function within the dorsal root ganglion.

In some instances, the pulse generator provides stimulation energy at a level which is capable of causing at least one blood vessel associated with the dorsal root ganglion to release an agent or send a cell signal which affects a neuron or glial cell within the dorsal root ganglion.

And, in some embodiments, the lead is configured to be advanced in an antegrade direction through an epidural space and positioned so that at least a portion of the lead extends along a nerve root sleeve angulation.

Other objects and advantages of the present invention will become apparent from the detailed description to follow, together with the accompanying drawings.

BRIEF DESCRIPTION OF THE DRAWINGS

FIG. 1A provides a schematic illustration of a spinal cord, associated nerve roots and a peripheral nerve on a spinal level and FIG. 1B illustrates cells within a DRG.

FIG. 9 provides a schematic illustration of an embodiment of the lead positioned on a DRG, including various cells and anatomical structures associated with the DRG.

FIGS. 10A-10D, 11, 12 illustrate embodiments of a lead and delivery system.

DETAILED DESCRIPTION OF THE INVENTION

The present invention provides devices, systems and methods for treating pain while minimizing or eliminating possible complications and undesired side effects, particularly the sensation of paresthesia. This is achieved by stimulating in proximity to a dorsal root ganglion with stimulation energy in a manner that will affect pain sensations without generating substantial sensations of paresthesia. In some embodiments, such neurostimulation takes advantage of anatomical features and functions particular to the dorsal root ganglion, as will be described in more detail below. The devices, systems and methods are minimally invasive, therefore reducing possible complications resulting from the implantation procedure, and targeted so as to manage pain sensations with minimal or no perceptions such as paresthesia.

Figure 2A:
FIGS. 2A-2C provide a cross-sectional histological illustration of a spinal cord and a DRG under varying levels of magnification.
Figure 2B:
Figure 2C:
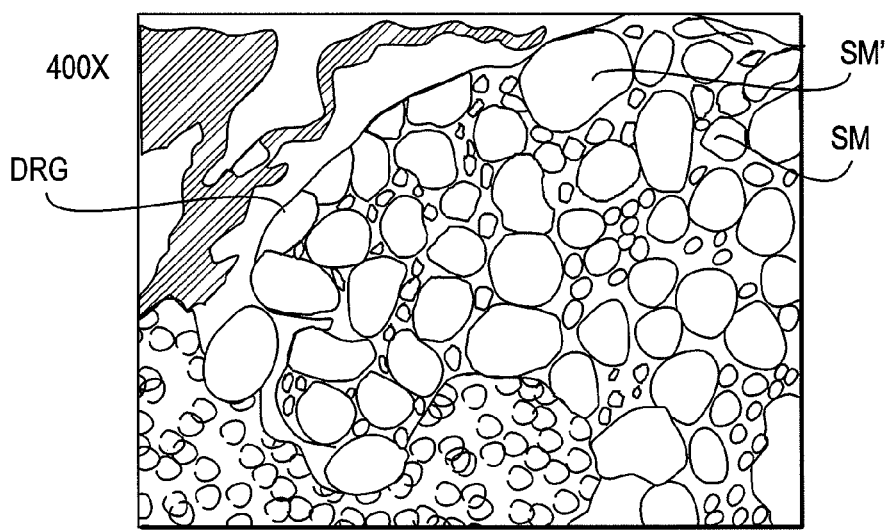

FIG. 1A provides a schematic illustration of a spinal cord S, associated nerve roots and a peripheral nerve on a spinal level. Here, the nerve roots include a dorsal root DR and a ventral root VR that join together at the peripheral nerve PN. The dorsal root DR includes a dorsal root ganglion DRG, as shown. The DRG is comprised of a variety of cells, including large neurons, small neurons and non-neuronal cells. Each neuron in the DRG is comprised of a bipolar or quasi-unipolar cell having a soma (the bulbous end of the neuron which contains the cell nucleus) and two axons. The word soma is Greek, meaning "body"; the soma of a neuron is often called the "cell body". Somas are gathered within the DRG, rather than the dorsal root, and the associated axons extend therefrom into the dorsal root and toward the peripheral nervous system. FIG. 1B provides an expanded illustration of cells located in the DRG, including a small soma SM, a large soma SM' and non-neuronal cells (in this instance, satellite cells SC). FIGS. 2A-2C provide a cross-sectional histological illustration of a spinal cord S and associated nerve roots, including a DRG. FIG. 2A illustrates the anatomy under 40× magnification and indicates the size relationship of the DRG to the surrounding anatomy. FIG. 2B illustrates the anatomy of FIG. 2A under 100× magnification. Here, the differing structure of the DRG is becoming visible. FIG. 2C illustrates the anatomy of FIG. 2A under 400× magnification focusing on the DRG. As shown, the larger soma SM' and the smaller somas SM are located within the DRG.

In some embodiments, stimulation of a DRG according to the present invention is achieved with the use of a lead having at least one electrode thereon. The lead is advanced through the patient anatomy so that the at least one electrode is positioned on, near, about or in proximity to the target DRG. The lead and electrode(s) are sized and configured so that the electrode(s) are able to minimize or exclude undesired stimulation of other anatomies.

Figure 3:
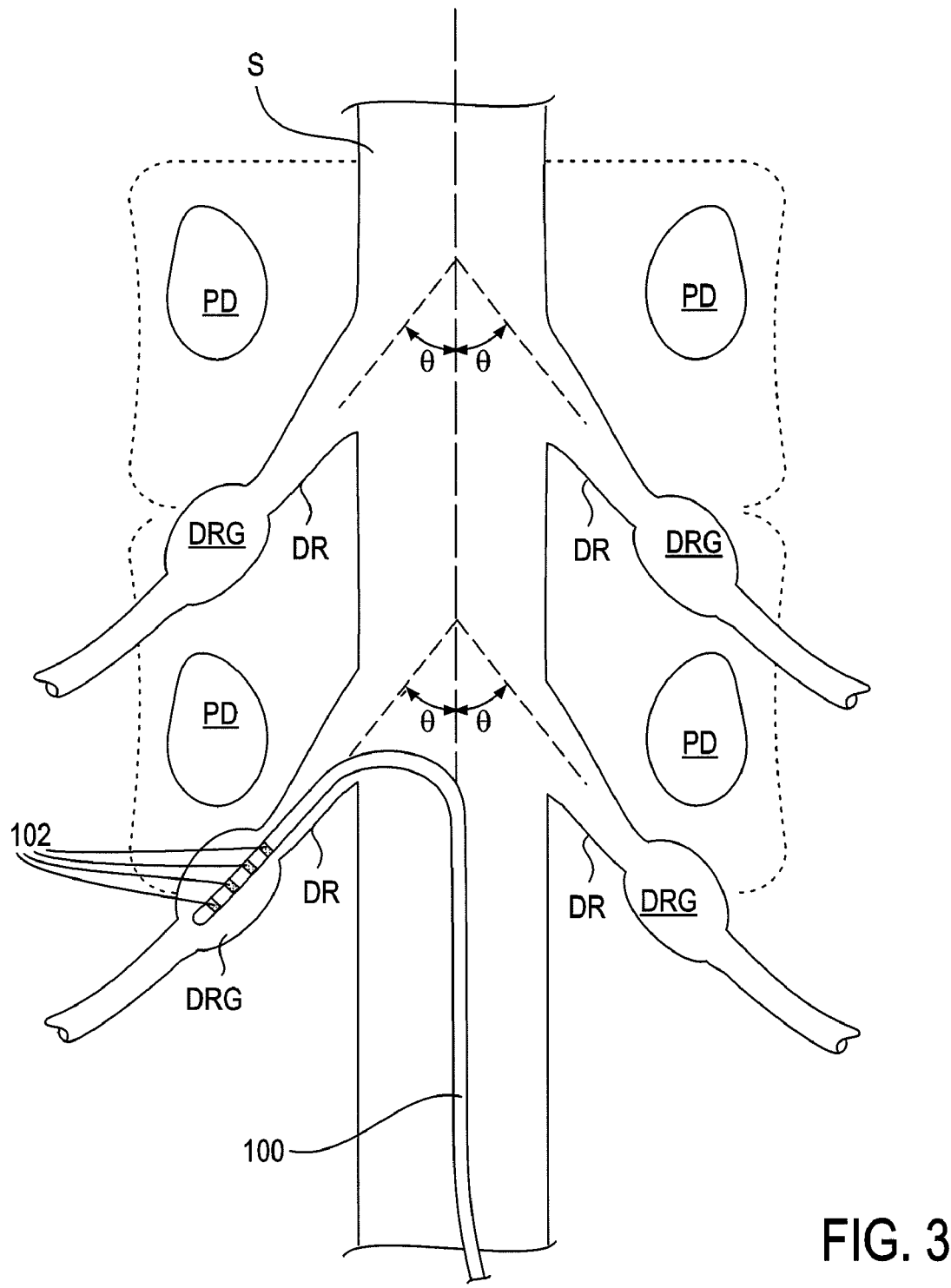
FIG. 3 illustrates an embodiment of a lead, having at least one electrode thereon, advanced through the patient anatomy so that at least one of the electrodes is positioned on a target DRG.

FIG. 3 illustrates an embodiment of a lead 100, having at least one electrode 102 thereon, advanced through the patient anatomy so that at least one of the electrodes 102 is positioned on a target DRG. In this example, the lead 100 is inserted epidurally and advanced in an antegrade direction along the spinal cord S. As shown, each DRG is disposed along a dorsal root DR and typically resides at least partially between the pedicles PD or within a foramen. Each dorsal root DR exits the spinal cord S at an angle θ. This angle θ is considered the nerve root sleeve angulation and varies slightly by patient and by location along the spinal column. However, the average nerve root angulation is significantly less than 90 degrees and typically less than 45 degrees. Therefore, advancement of the lead 100 toward the target DRG in this manner involves making a sharp turn along the angle θ. A turn of this severity is achieved with the use of delivery tools and design features specific to such lead placement which will be described in more detail in later sections. In addition, the spatial relationship between the nerve roots, DRGs and surrounding structures are significantly influenced by degenerative changes, particularly in the lumbar spine. Thus, patients may have nerve root angulations which differ from the normal anatomy, such as having even smaller angulations necessitating even tighter turns. The delivery tools and devices accommodate these anatomies.

Figure 4:
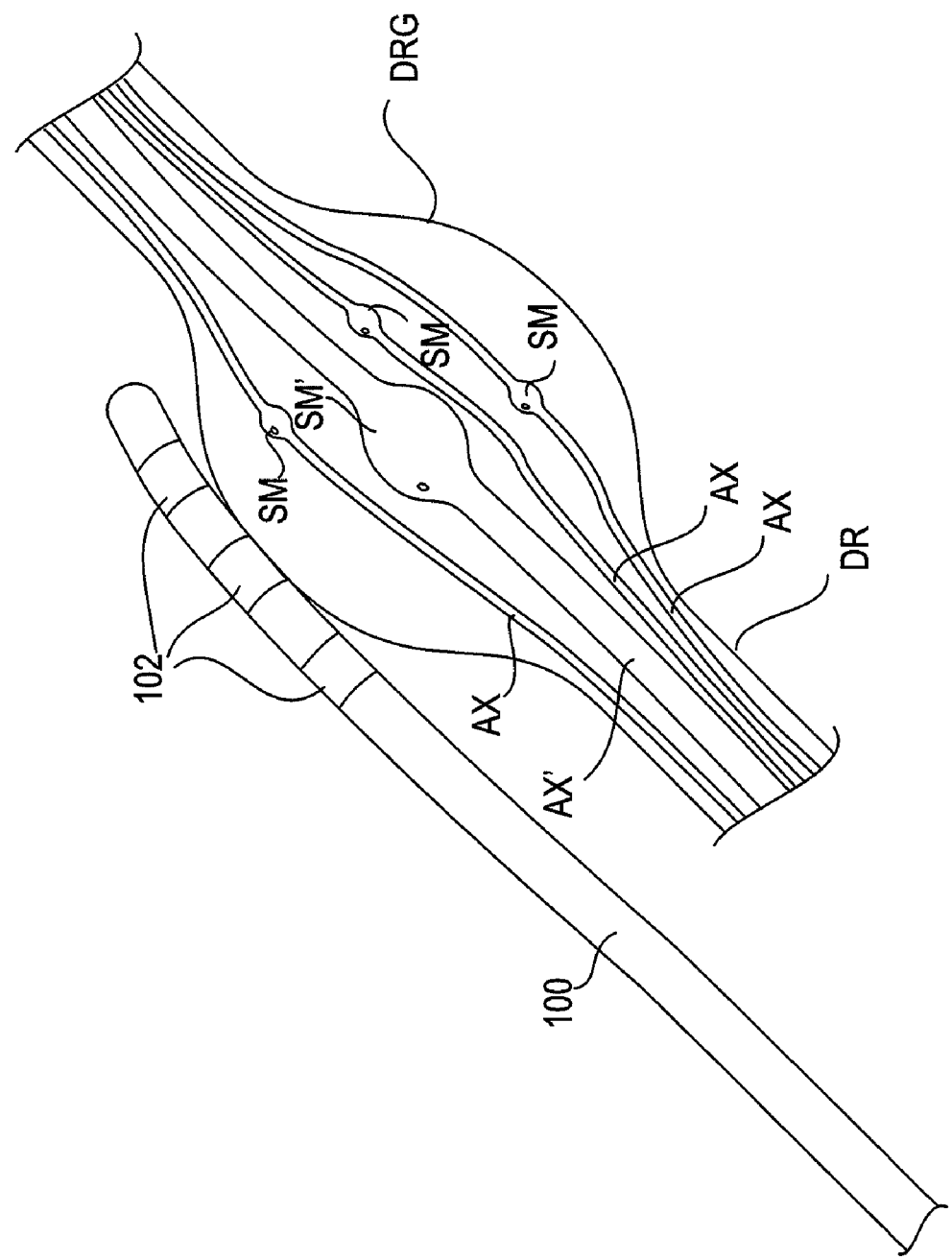
FIG. 4 provides a schematic illustration of the lead positioned on a DRG.
Figure 5:
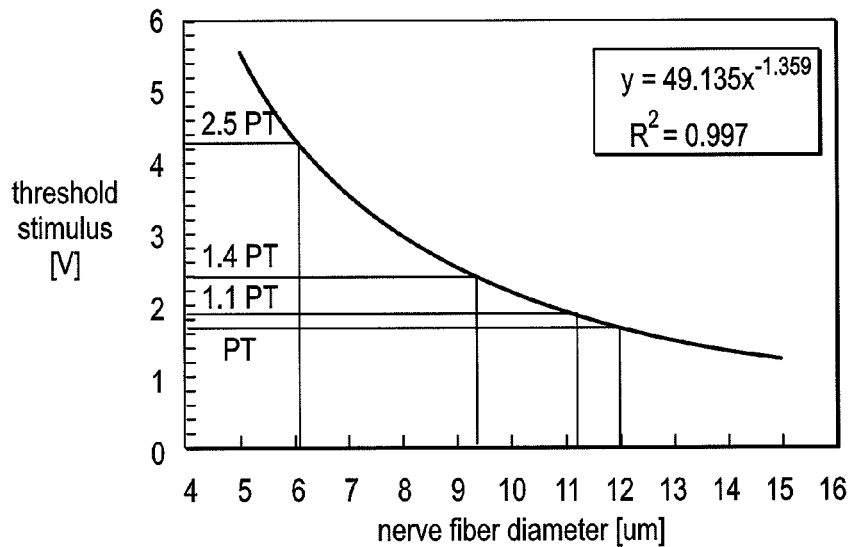
FIG. 5 illustrates a graph showing an example relationship between threshold stimulus and nerve fiber diameter.
Figure 6:
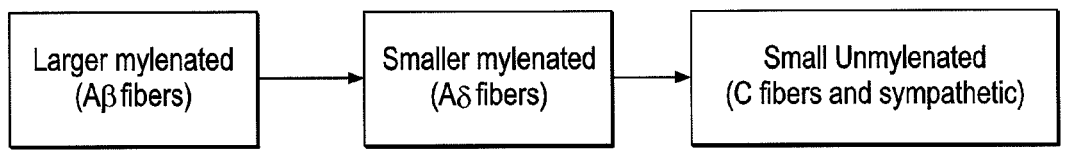
FIG. 6 illustrates recruitment order based on nerve fiber diameter.

FIG. 4 provides a schematic illustration of an embodiment of the lead 100 positioned on a DRG. As illustrated, the DRG includes smaller somas SM and larger somas SM'. Each soma is connected with an associated axon or nerve fiber which extends through the root. The axon or nerve fiber is a long, slender projection of a nerve cell, or neuron that conducts electrical impulses away from the neuron's cell body or soma. The smaller somas SM have smaller axons AX and the larger somas SM' have larger axons AX'. Typically, axons or nerve fibers are recruited electrically according to size. Referring to FIG. 5, a graph is provided which illustrates an example relationship between threshold stimulus and nerve fiber diameter. Generally, as the nerve fiber diameter increases, the threshold stimulus decreases. Thus, as illustrated in FIG. 6, larger mylenated fibers (Aβ fibers) are recruited before smaller mylenated fibers (Aδ fibers), which are in turn recruited before small unmylenated fibers (C fibers).

Figure 7:
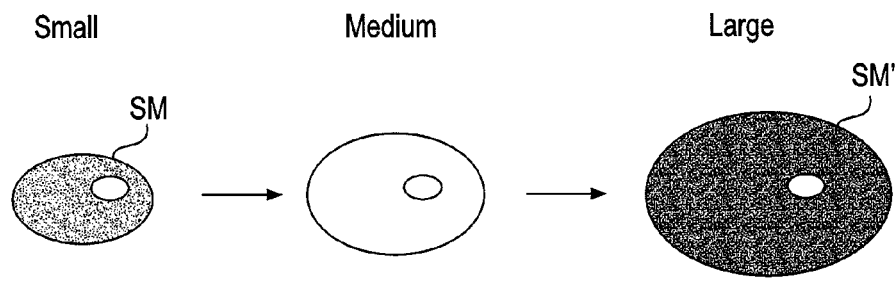
FIG. 7 illustrates recruitment order based on cell body size.
Figure 8:
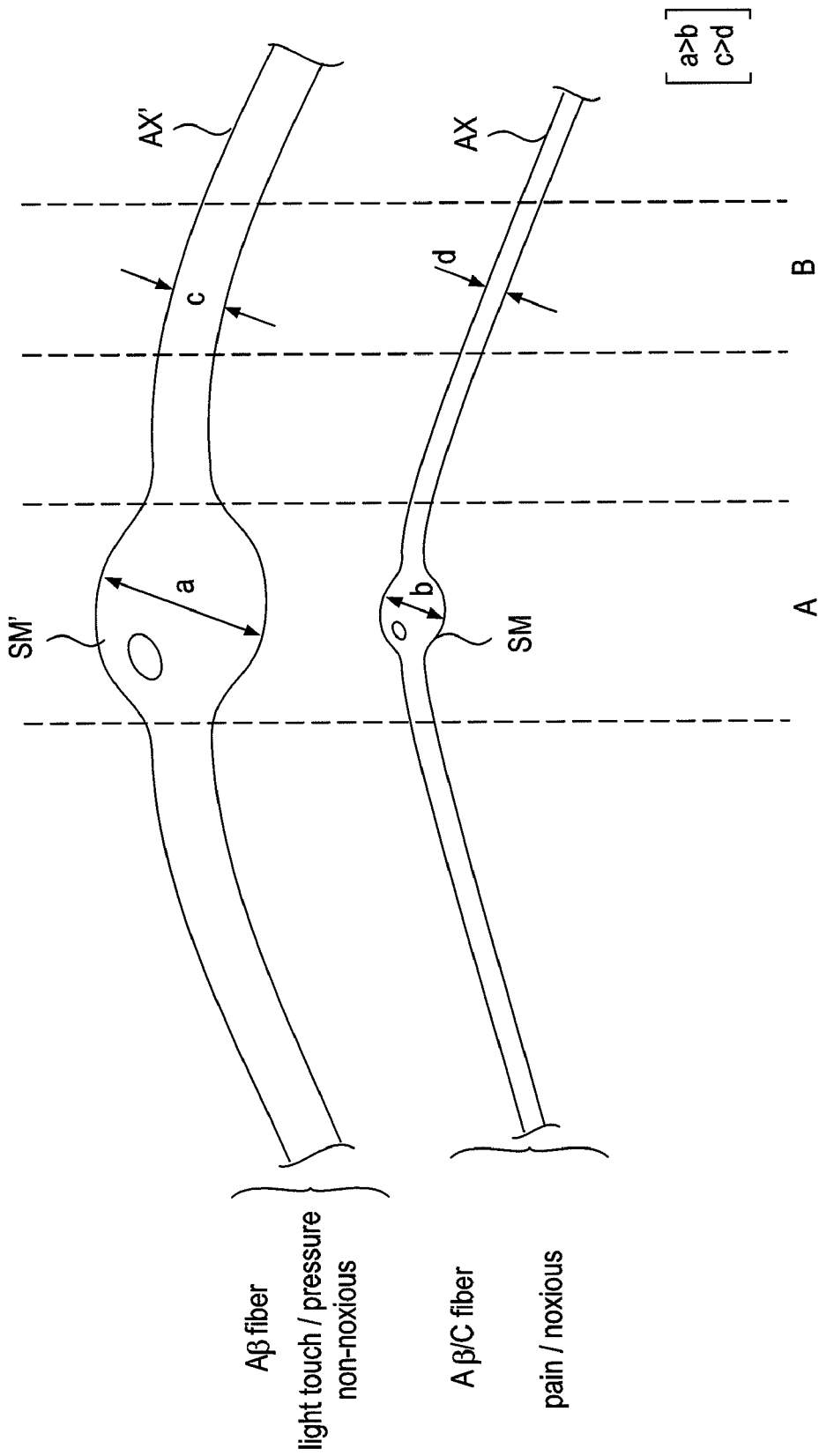
FIG. 8 illustrates recruitment order differences based on location of stimulation.

Referring to FIG. 7, the opposite is true of cell bodies compared to nerve fibers. Generally, it takes less current to recruit or modulate a smaller cell body or soma membrane than a larger one. Thus, as shown in FIG. 8, when low stimulation is provided in region A (to the cell bodies SM', SM) the smaller diameter cell bodies SM are selectively stimulated before the larger diameter cell bodies SM'. This is due to the relatively smaller charge it takes to effectively modulate membrane function of a smaller cell body. However, when low stimulation is provided in region B (to the axons AX', AX) the larger axons AX' are stimulated before the smaller axons AX. Referring back to FIG. 4, since the cell bodies or somas are located within the DRG, region A generally corresponds to the DRG and region B generally corresponds to the dorsal root DR.

When a patient experiences pain, the nociceptive or painful stimuli are transduced from peripheral structures to the central nervous systems through small diameter, thinly myelinated and unmyelinated afferent nerve fibers or axons AX. Electrically, these fibers are more difficult to selectively target since larger diameter fibers or axons AX' are preferentially activated by electrical currents based upon the above described size principle. These larger fibers AX' are associated with sensory stimuli such as light touch, pressure and vibration and well as paresthesia such as generated by SCS.

The present invention provides methods and devices for preferentially neuromodulating the smaller diameter axon/smaller soma neurons over the larger diameter axon/larger soma neurons. This in turn interrupts pain transmission while minimizing or eliminating paresthesia. Referring again to FIG. 4, an example is illustrated of a lead 100 positioned so that at least one of the electrodes 102 is disposed so as to selectively stimulate the DRG while minimizing or excluding undesired stimulation of other anatomies, such as portions of the dorsal root DR. This allows the smaller diameter axon/smaller soma neurons to be recruited before the larger diameter axon/larger soma neurons. Consequently, these neurons involved in pain transduction can be modulated without producing paresthesias. This is achieved with the use of less current or lower power stimulation, i.e. stimulation at a sub-threshold level to paresthesia. The effect of this preferential, targeted neuromodulation is analgesia without resultant paresthesias. In addition, lower power stimulation means lower power consumption and longer battery life.

Conventional spinal stimulation systems typically provide stimulation with a frequency of about 30-120 Hz. In contrast, therapeutic benefits have been achieved with the devices and methods described herein at stimulation frequencies below those used in conventional stimulation systems. In one aspect, the stimulation frequency used for the DRG stimulation methods described herein is less than 25 Hz. In other aspects, the stimulation frequency could be even lower such as in the range of less than 15 Hz. In still other aspects, the stimulation frequency is below 10 Hz. In one specific embodiment, the stimulation frequency is 5 Hz. In another specific, embodiment, the stimulation frequency is 2 Hz. In addition to lower stimulation frequencies, other stimulation patterns for the inventive devices and methods are also lower than those used in conventional stimulation systems. For example, embodiments of the present invention have achieved repeatable dermatome specific pain relief using a stimulation signal having an amplitude of less than 500 microamps, a pulse width of less than 120 microseconds and a low stimulation frequency as discussed above. It is believed that embodiments of the present invention can achieve dermatome specific pain relief using signals having pulse widths selected within the range of 60 microseconds to 120 microseconds. It is believed that embodiments of the present invention can achieve dermatome specific pain relief using a signal having an amplitude of about 200 microamps. In one specific example, repeatable dermatome specific pain relief was achieved in an adult female using a signal with an amplitude of 200 microamps, a pulse width of 60 microseconds and a frequency of 2 Hz. It may also be appreciated that other suitable stimulation signal parameters may be used along, such as provided in U.S. patent application Ser. No. 12/607,009 entitled "Selective Stimulation Systems and Signal Parameters For Medical Conditions", filed Oct. 27, 2009, incorporated herein by reference for all purposes.

In addition to neuronal cells, non-neuronal cells, such as glial cells, are located within the DRG. Glial cells surround neurons, hold them in place, provide nutrients, help maintain homeostasis, provide electrical insulation, destroy pathogens, regulate neuronal repair and the removal dead neurons, and participate in signal transmission in the nervous system. In addition, glial cells help in guiding the construction of the nervous system and control the chemical and ionic environment of the neurons. Glial cells also play a role in the development and maintenance of dysfunction in chronic pain conditions. A variety of specific types of glial cells are found within the DRG, such as satellite cells and Schwann cells.

Satellite cells surround neuron cell bodies within the DRG. They supply nutrients to the surrounding neurons and also have some structural function. Satellite cells also act as protective, cushioning cells. In addition, satellite cells can form gap junctions with neurons in the DRG. As opposed to classical chemical transmission in the nervous system, gap junctions between cells provide a direct electrical coupling. This, in turn, can produce a form of a quasi glial-neuronal syncytium. Pathophysiologic conditions can change the relationship between glia and cell bodies such that the neurons transducting information about pain can become dysfunctional. Therefore neurostimulation of the DRG can not only directly affect neurons but also impact the function of glial cells. Modulation of glial cell function with neurostimulation can in turn alter neuronal functioning. Such modulation can occur at levels below a threshold for generating sensations of paresthesia.

FIG. 9 provides a schematic illustration of an embodiment of the lead 100 positioned on a DRG. As illustrated, the DRG includes satellite cells SC surrounding smaller somas SM and larger somas SM'. In some embodiments, stimulation energy provided by at least one of the electrodes 102 neuromodulates satellite cells SC. Such neuromodulation impacts their function and, secondarily, impacts the function of associated neurons so as to interrupt or alter processing of sensory information, such as pain. Consequently, DRG satellite cell neuromodulation can be a treatment for chronic pain.

Another type of glial cells are Schwann cells. Also referred to as neurolemnocytes, Schwann cells assist in neuronal survival. In myelinated axons, Schwann cells form the myelin sheath. The vertebrate nervous system relies on the myelin sheath for insulation and as a method of decreasing membrane capacitance in the axon. The arrangement of the Schwann cells allows for saltatory conduction which greatly increases speed of conduction and saves energy. Non-myelinating Schwann cells are involved in maintenance of axons. Schwann cells also provide axon support, trophic actions and other support activities to neurons within the DRG.

Referring again to FIG. 9, Schwann cells SWC are illustrated along the axons of a neuron within the DRG. In some embodiments, stimulation energy provided by at least one of the electrodes 102 of the lead 100 neuromodulates Schwann cells SWC. Such neuromodulation impacts their function and, secondarily, impacts the function of associated neurons. Neuromodulation of Schwann cells impacts neuronal processing, transduction and transfer of sensory information including pain. Thus, DRG stimulation relieves pain in the short and long term by impacting function of Schwann cells. This also may be achieved at stimulation levels below a threshold for generating sensations of paresthesia.

Beyond the neural cells (neurons, glia, etc) that are present in the DRG, there is a rich network of blood vessels that travel in and about the DRG to encapsulate the DRG and provide a blood supply and oxygen to this highly metabolically active neural structure. FIG. 9 schematically illustrates a blood vessel BV associated with and an example DRG. In some embodiments, stimulation energy is provided by at least one of the electrodes 102 of the lead 100. Stimulation of the DRG can cause the release of a variety of agents from the neurons, glia and/or blood vessels which ultimately impact the function of neurons involved in the transduction and processing of sensory information, including pain. For example, in some embodiments stimulation of the DRG causes one or more types of neurons and/or one or more types of glial cells to release vasoactive agents which affect at least one blood vessel. The at least one blood vessel in turn releases neuronal agents impact the function of neurons in processing pain. Or, the at least one blood vessel releases glial active agents which indirectly impacts the function of neurons in processing pain. In other embodiments, stimulation of the DRG directly affects the associated blood vessels which provide vessel to neuron cell signaling or vessel to glial cell signaling. Such cell signaling ultimately impacts neuronal function, such as by altering metabolic rate or inducing the release of neural responsive chemicals which, in turn, directly change the cell function. The change in cell function induces analgesia or pain relief in the short-term, mid-term and long-term. Such changes may occur at stimulation levels below a threshold for generating sensations of paresthesia.

Desired positioning of a lead 100 near the target anatomy, such as the DRG, may be achieved with a variety of delivery systems, devices and methods. Referring back to FIG. 3, an example of such positioning is illustrated. In this example, the lead 100 is inserted epidurally and advanced in an antegrade direction along the spinal cord S. As shown, each DRG is disposed along a dorsal root DR and typically resides at least partially between the pedicles PD or within a foramen. Each dorsal root DR exits the spinal cord S at an angle θ. This angle θ is considered the nerve root sleeve angulation and varies slightly by patient and by location along the spinal column. However, the average nerve root angulation is significantly less than 90 degrees and typically less than 45 degrees. Therefore, advancement of the lead 100 toward the target DRG in this manner involves making a sharp turn along the angle θ. In addition, the spatial relationship between the nerve roots, DRGs and surrounding structures are significantly influenced by degenerative changes, particularly in the lumbar spine. Thus, patients may have nerve root angulations which differ from the normal anatomy, such as having even smaller angulations necessitating even tighter turns. Turns of this severity are achieved with the use of delivery tools having design features specific to such lead placement.

Referring to FIGS. 10A-10D, an example lead and delivery devices for accessing a target DRG are illustrated. FIG. 10A illustrates an embodiment of a lead 100 comprising a shaft 103 having a distal end 101 with four electrodes 102 disposed thereon. It may be appreciated that any number of electrodes 102 may be present, including one, two, three, four, five, six, seven, eight or more. In this embodiment, the distal end 101 has a closed-end distal tip 106. The distal tip 106 may have a variety of shapes including a rounded shape, such as a ball shape (shown) or tear drop shape, and a cone shape, to name a few. These shapes provide an atraumatic tip for the lead 100 as well as serving other purposes. The lead 100 also includes a stylet lumen 104 which extends toward the closed-end distal tip 106. A delivery system 120 is also illustrated, including a sheath 122 (FIG. 10B), stylet 124 (FIG. 10C) and introducing needle 126 (FIG. 10D).

Referring to FIG. 10B, an embodiment of a sheath 122 is illustrated. In this embodiment, the sheath 122 has a distal end 128 which is pre-curved to have an angle α, wherein the angle α is in the range of approximately 80 to 165 degrees. The sheath 122 is sized and configured to be advanced over the shaft 103 of the lead 100 until a portion of its distal end 128 abuts the distal tip 106 of the lead 100, as illustrated in FIG. 11. Thus, the ball shaped tip 106 of this embodiment also prevents the sheath 122 from extending thereover. Passage of the sheath 122 over the lead 100 causes the lead 100 to bend in accordance with the precurvature of the sheath 122. Thus, the sheath 122 assists in steering the lead 100 along the spinal column S and toward a target DRG, such as in a lateral direction.

Referring back to FIG. 10C, an embodiment of a stylet 124 is illustrated. The stylet 124 has a distal end 130 which is pre-curved so that its radius of curvature is in the range of approximately 0.1 to 0.5. The stylet 124 is sized and configured to be advanced within the stylet lumen 104 of the lead 100. Typically the stylet 124 extends therethrough so that its distal end 130 aligns with the distal end 101 of the lead 100. Passage of the stylet 124 through the lead 100 causes the lead 100 to bend in accordance with the precurvature of the stylet 124. Typically, the stylet 124 has a smaller radius of curvature, or a tighter bend, than the sheath 122. Therefore, as shown in FIG. 12, when the stylet 124 is disposed within the lead 100, extension of the lead 100 and stylet 124 through the sheath 122 bends or directs the lead 100 through a first curvature 123. Further extension of the lead 100 and stylet 124 beyond the distal end 128 of the sheath 122 allows the lead 100 to bend further along a second curvature 125. This allows the laterally directed lead 100 to now curve around toward the target DRG along the nerve root angulation. This two step curvature allows the lead 100 to be successfully positioned so that at least one of the electrodes 102 is on, near or about the target DRG, particularly by making a sharp turn along the angle θ.

Thus, the lead 100 does not require stiff or torqueable construction since the lead 100 is not torqued or steered by itself. The lead 100 is positioned with the use of the sheath 122 and stylet 124 which direct the lead 100 through the two step curvature. This eliminates the need for the operator to torque the lead 100 and optionally the sheath 122 with multiple hands. This also allows the lead 100 to have a lower profile as well as a very soft and flexible construction. This, in turn, minimizes erosion and discomfort created by pressure on nerve tissue, such as the target DRG and/or the nerve root, once the lead 100 is implanted. For example, such a soft and flexible lead 100 will minimize the amount of force translated to the lead 100 by body movement (e.g. flexion, extension, torsion).

Referring back to FIG. 10D, an embodiment of an introducing needle 126 is illustrated. The introducing needle 126 is used to access the epidural space of the spinal cord S. The needle 126 has a hollow shaft 127 and typically has a very slightly curved distal end 132. The shaft 127 is sized to allow passage of the lead 100, sheath 122 and stylet 124 therethrough. In some embodiments, the needle 126 is 14 gauge which is consistent with the size of epidural needles used to place conventional percutaneous leads within the epidural space. However, it may be appreciated that other sized needles may also be used, particularly smaller needles such as 16-18 gauge. Likewise, it may be appreciated that needles having various tips known to practitioners or custom tips designed for specific applications may also be used. The needle 126 also typically includes a Luer-Lok™ fitting 134 or other fitting near its proximal end. The Luer-Lok™ fitting 134 is a female fitting having a tabbed hub which engages threads in a sleeve on a male fitting, such as a syringe.

Methods of approaching a target DRG using such a delivery system 120 is further described and illustrated in U.S. Patent Application No. 61/144,690 filed Jan. 14, 2009, incorporated herein by reference for all purposes, along with examples of other delivery systems, devices and methods applicable to use with the present invention.

It may be appreciated that other types of leads and corresponding delivery systems may be used to position such leads in desired orientations to provide stimulation subthreshold to paresthesia. For example, the lead may have a pre-curved shape wherein the lead is deliverable through a sheath having a straighter shape, such as a substantially straight shape or a curved shape which is has a larger radius of curvature than the lead. Advancement of the lead out of the sheath allows the lead to recoil toward its pre-curved shape. Various combinations of curvature between the lead and sheath may allow for a variety of primary and secondary curvatures. Once the lead is desirably placed, the sheath may then be removed.

It may also be appreciated that a variety of approaches to the DRG may be used, such as an antegrade epidural approach, a retrograde epidural approach, a transforamenal approach or an extraforaminal approach (approaching along a peripheral nerve from outside of the spinal column), and a contralateral approach, to name a few. Likewise, the at least one electrode may be positioned in, on or about, in proximity to, near or in the vicinity of the DRG.

Although the foregoing invention has been described in some detail by way of illustration and example, for purposes of clarity of understanding, it will be obvious that various alternatives, modifications, and equivalents may be used and the above description should not be taken as limiting in scope of the invention which is defined by the appended claims.

What is claimed is:

1. A method of treating pain in a patient comprising:
   positioning a lead having at least one electrode disposed thereon so that at least one of the at least one electrode is in proximity to a dorsal root ganglion; and
   providing stimulation energy to the at least one of the at least one electrode so as to stimulate at least a portion of the dorsal root ganglion,
   wherein together the positioning of the lead step and the providing stimulation energy step reduce pain sensations without generating sensations of paresthesia.

2. A method as in claim 1, wherein providing stimulation energy comprises providing stimulation energy at a level below a threshold for Aβ fiber recruitment.

3. A method as in claim 2, wherein providing stimulation energy comprises providing stimulation energy at a level below a threshold for Aβ fiber cell body recruitment.

4. A method as in claim 3, wherein providing stimulation energy comprises providing stimulation energy at a level above a threshold for M fiber cell body modulation.

5. A method as in claim 3, wherein providing stimulation energy comprises providing stimulation energy at a level above a threshold for C fiber cell body modulation.

6. A method as in claim 3, wherein providing stimulation energy comprises providing stimulation energy at a level above a threshold for small myelenated fiber cell body modulation.

7. A method as in claim 3, wherein providing stimulation energy comprises providing stimulation energy at a level above a threshold for unmyelenated fiber cell body modulation.

8. A method as in claim 1, wherein providing stimulation energy comprises providing stimulation energy at a level which is capable of modulating glial cell function within the dorsal root ganglion.

9. A method as in claim 8, wherein providing stimulation energy comprises providing stimulation energy at a level which is capable of modulating satellite cell function within the dorsal root ganglion.

10. A method as in claim 8, wherein providing stimulation energy comprises providing stimulation energy at a level which is capable of modulating Schwann cell function within the dorsal root ganglion.

11. A method as in claim 1, wherein providing stimulation energy comprises providing stimulation energy at a level which is capable of causing at least one blood vessel associated with the dorsal root ganglion to release an agent or send a cell signal which affects a neuron or glial cell within the dorsal root ganglion.

12. A method as in claim 1, wherein positioning the lead comprises advancing the lead through an epidural space so that at least a portion of the lead extends along a nerve root sleeve angulation.

13. A method as in claim 12, wherein advancing the lead through the epidural space comprises advancing the lead in an antegrade direction.

14. A method of treating a patient comprising:
selectively electrically stimulating a small fiber cell body within a dorsal root ganglion of the patient while excluding an Aβ fiber cell body within the dorsal root ganglion of the patient.

15. A method as in claim 14, wherein the small fiber body comprises a M fiber cell body.

16. A method as in claim 14, wherein the small fiber body comprises a C fiber cell body.

17. A method of treating a patient comprising:
identifying a dorsal root ganglion associated with a sensation of pain by the patient; and
electrically neuromodulating at least one glial cell within the dorsal root ganglion so as to reduce the sensation of pain by the patient.

18. A method as in claim 17, wherein the at least one glial cell comprises a satellite cell.

19. A method as in claim 17, wherein the at least one glial cell comprises a Schwann cell.

20. A method as in claim 17, wherein neuromodulating comprises providing stimulation at a level that reduces the sensation of pain without generating substantial sensations of paresthesia.

21. A method of treating a patient comprising:
positioning a lead having at least one electrode disposed thereon so that at least one of the at least one electrode is in proximity to a dorsal root ganglion; and
providing stimulation energy to the at least one electrode so as to stimulate at least one blood vessel associated with the dorsal root ganglion in a manner that causes the at least one blood vessel to release an agent which neuromodulates a neuron within the dorsal root ganglion.

22. A method as in claim 21, wherein the agent comprises a neuromodulatory chemical that affects the function of neurons involved in pain sensory transduction.

* * * * *